United States Patent [19]
Nickel et al.

[11] Patent Number: 6,093,704
[45] Date of Patent: *Jul. 25, 2000

[54] USE OF DOPAMINE RECEPTOR ANTAGONISTS IN PALLIATIVE TUMOR THERAPY

[75] Inventors: Bernd Nickel, Muhltal; Peter Hilgard, Frankfurt; Thomas Klenner, Ingelheim; Jürgen Engel, Alzenau, all of Germany

[73] Assignee: ASTA Medica Aktiengesellschaft, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/986,235

[22] Filed: Dec. 5, 1997

[30] Foreign Application Priority Data

Dec. 6, 1996 [DE] Germany .......................... 196 50 778

[51] Int. Cl.$^7$ ....................... A61K 31/685; A61K 31/445
[52] U.S. Cl. ............................... 514/77; 514/322
[58] Field of Search ....................... 514/322, 77

[56] References Cited

PUBLICATIONS

Willis et al., Pharmacol., Biochem. Behav., 31(1), 69–73 Abstract Only, 1988.
Frussa–Filho et al., Braz. J. Med. Biol. Res., 24(6), 611–14 Abstract Only, 1991.
Spruss et al., J. Cancer Res. Clin. Oncol., 119(3), 142–9 Abstract Only, 1993.

"A dose–finding study of miltefosine (hexadecylphosphocholine) in patients with metastatic solid tumours"; Verweij, J., Planting, A., van der Burg, M., Stoter, G.; Department of Medical Oncology, Rotterdam Cancer Institute/Daniel den Hoed Kliniek, The Netherlands; J Cancer Res Clin Oncol 1992; 118(8):606–8. Abstract only.

"Phase II study of daily oral miltefosine (hexadecylphosphocholine) in advanced colorectal cancer"; Planting AS, Stoter, G., Verweij, J.; Department of Medical Oncology, Rotterdam Cancer Institute/Dr. Daniel den Hoed Kliniek, The Netherlands; Eur J. Cancer 1993;29A(4):518–9. Abstract only.

Rote Liste 1998; Arzneimittelverzeichnis des Bundesverbandes der Pharmazeutischen Industrie e.V. (BPI), des Verbandes Forschender Arzneimittelhersteller e.V. (VFA), des Bundesfachverbandes der Arzneimittel–Hersteller e.V. (BAH) und des Verbandes aktiver Pharmaunternehmen e.V. (VAP); ECV, Editio Cantor, Aulendorf/Wurtt. Abstract only.

"Effects of domperidone in patients with chronic unexplained upper gastrointestinal symptoms: a double–blind, placebo–controlled study"; Davis RH, Clench MH, Mathias JR; Department of Medicine, College of Medicine, University of Florida, Gainesville; Dig Dis Sci 1988 Dec; 33(12):1505–11. Abstract only.

*Primary Examiner*—Jerome D. Goldberg
*Attorney, Agent, or Firm*—Cushman Darby & Cushman IP Group of Pillsbury Madison & Sutro LLP

[57] ABSTRACT

The side effect of decrease in body weight caused by the alkylphosphocholines such as miltefosine can be antagonized by certain acetylcholine receptor antagonists such as domperidone and pimozide. The combination of alkylphosphocholine plus the antagonist does not have any effect on the anti-tumor action of the alkylphosphocholine. The combination also caused no new side effects in the animals.

8 Claims, 12 Drawing Sheets

USE OF DOPAMINE RECEPTOR ANTAGONISTS IN PALLIATIVE TUMOR THERAPY

CROSS-REFERENCE TO RELATED APPLICATION

This application claim priority from German Application No. 19650778.2, filed on Dec. 6, 1996, the subject matter of which is hereby incorporated herein by reference.

BACKGROUND OF THE INVENTION

1. Field of the Invention

The invention relates to the use of dopamine receptor antagonists in palliative tumor therapy, particularly as agents for antagonizing side effects such as are frequently observed in tumor therapy by means of alkylphosphocholines, particularly miltefosine.

2. Background Information

It is known and described that the alkylphosphocholine miltefosine causes side effects in patients during the treatment of cancer. These also manifest themselves in patients treated with miltefosine by a marked loss of body weight (*Eur. J. Cancer*, Vol. 29 A, No. 2, pp. 208–209, 1993). Further side effects of the chemotherapy are: damage to the tissue with a high proliferation rate, leuko- and thrombopenia, decrease in erythrocytes, gastrointestinal disorders, loss of appetite, upper abdominal complaints, disturbed absorption and diarrhea, as well as loss of hair and also liver damage and hyperuricaemia.

In a dose-finding study by J. Verweij et al. (*J. Cancer Res. Clin. Oncol* 118:606–608 (1992)), it was observed that most antiemetics (including $5HT_3$ antagonists) were inactive in the prevention of vomiting and nausea. The smallest emetic effect was achieved if miltefosine was taken immediately after eating, domperidone being given 0.5 hours before eating in a dose of 20 mg. In the phase II studies of the same author which were carried out later (*Eur. J. Cancer Vol.* 29 A, No. 5 p. 779(1993), it was meanwhile found that it was not possible to prevent vomiting either by standard antiemetics or by $5HT_3$ antagonists.

Since the loss of weight under tumor treatment with alkylphosphocholines leads to a further weakening of the already overloaded body, it was the object of the invention to characterize substances which, in combination with miltefosine or its derivatives, antagonize the known side effects of the alkylphosphocholines such as decrease in body weight.

It must be ensured here that the anti-tumor action of miltefosine or its derivatives is not abolished or reduced by combination with the antidote and no additional side effects occur due to the administration of the combination.

SUMMARY OF THE INVENTION

The above object has now been achieved in that agents for antagonizing side effects such as are frequently observed during tumor therapy by means of alkylphosphocholines, in particular miltefosine, have been found and prepared. These are dopamine receptor antagonists, particularly the two dopamine antagonists domperidone and pimozide. It is to be understood that these agents can be administered both in a fixed combination with the alkylphosphocholine and, in each case, in individual packs and sequentially.

DETAILED DESCRIPTION OF THE INVENTION

EXAMPLE

Experimental results

Figure 1:
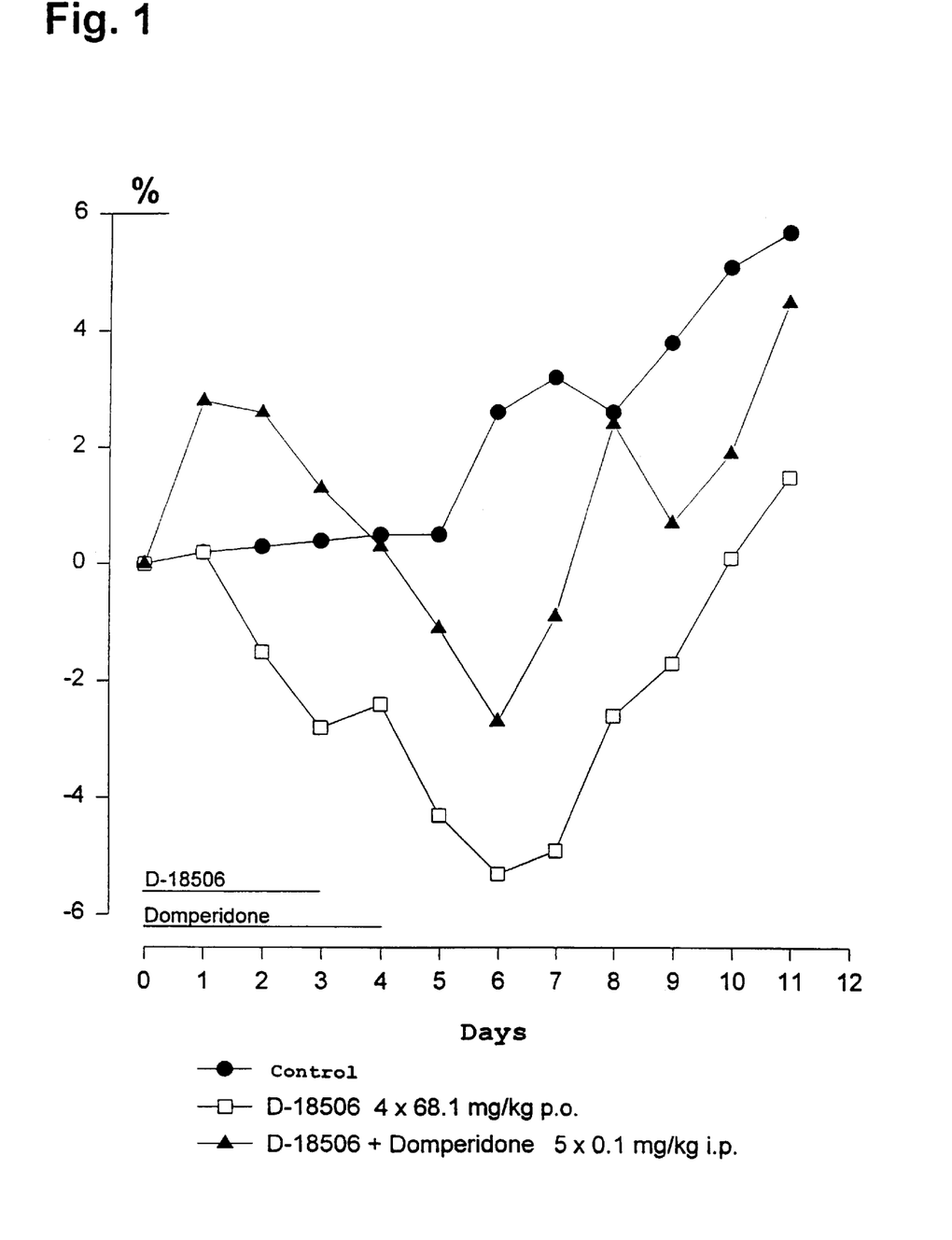
FIG. 1 shows effects of D-18506 (miltefosine) and domperidone on the body weight of normal rats.
Figure 2:
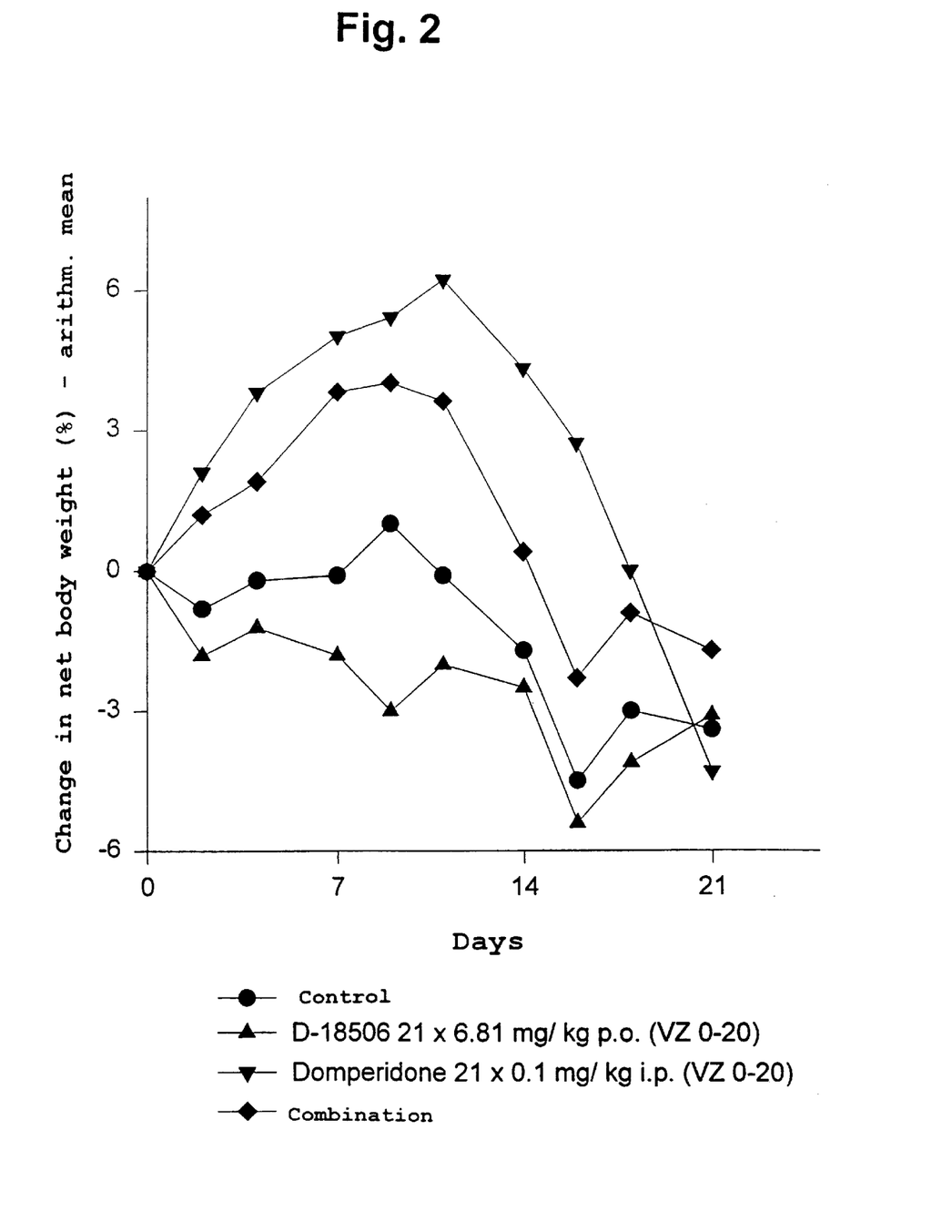
FIG. 2 shows effects of D-18506 (miltefosine) and domperidone on the body weight of rats with DM1A-induced breast tumor.
Figure 3:
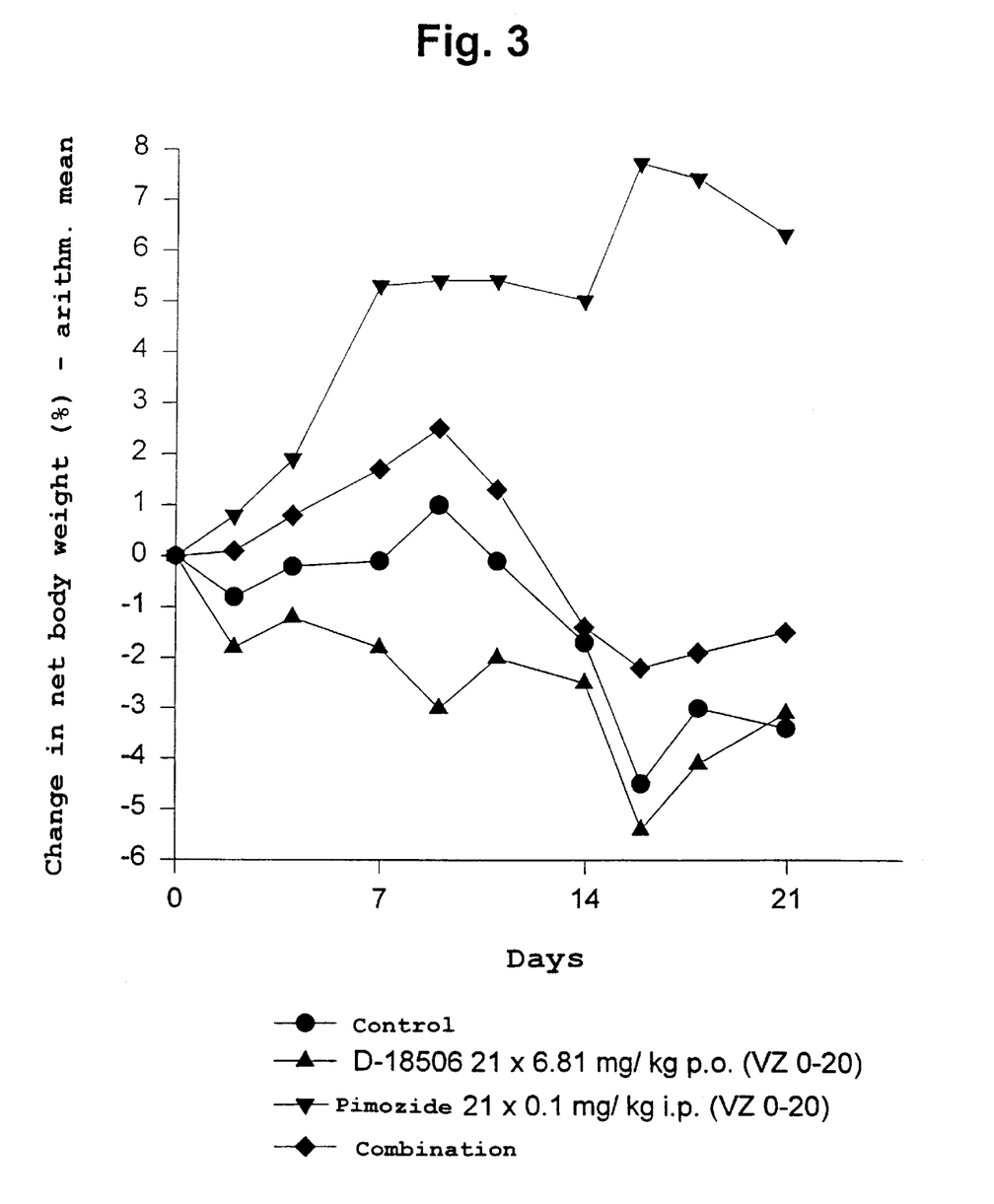
FIG. 3 shows effects of D-18506 (miltefosine) and pimozide on the body weight of rats with DMBA-induced breast tumor.
Figure 4:
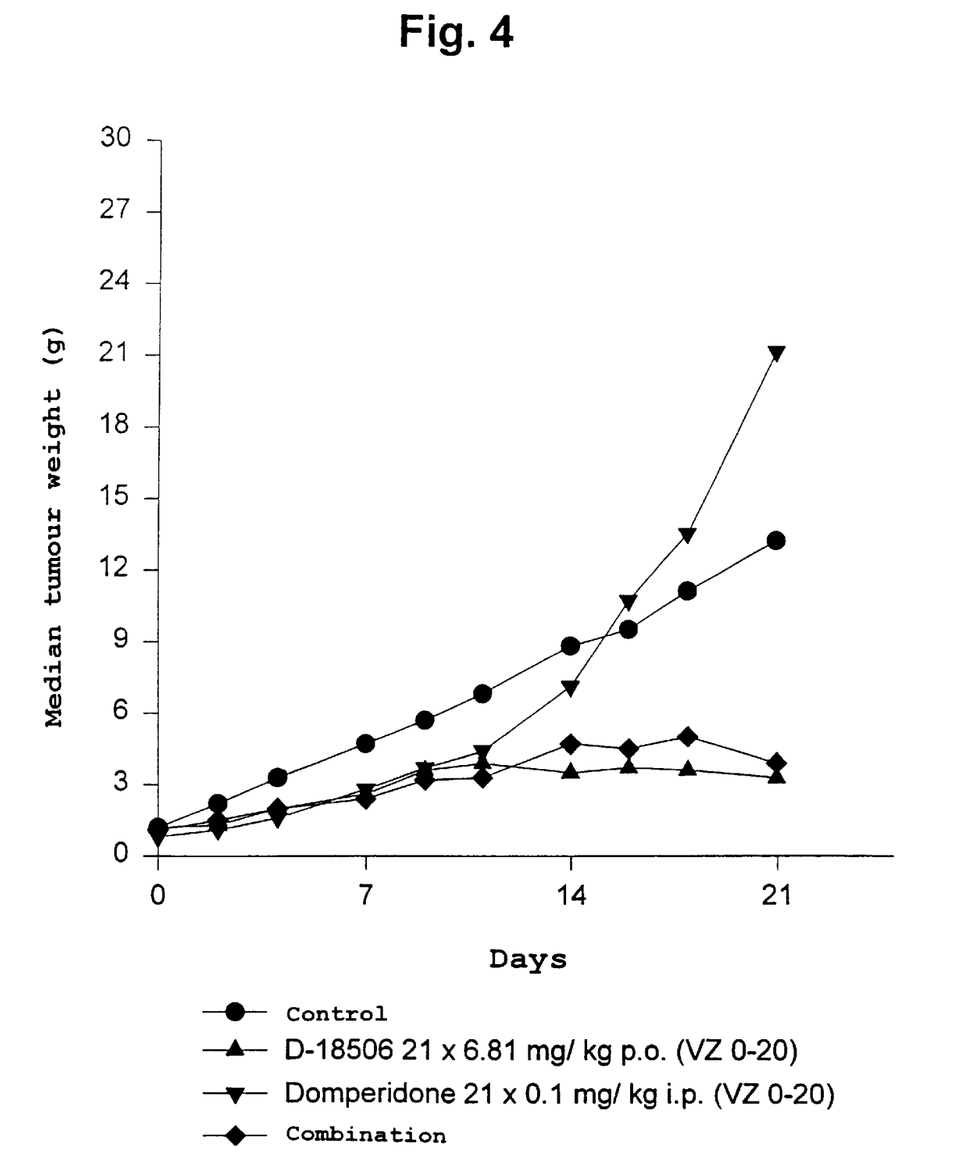
FIG. 4 shows effects of D-18506 (miltefosine) and domperidone on DMBA-induced breast tumor of rats.
Figure 5:
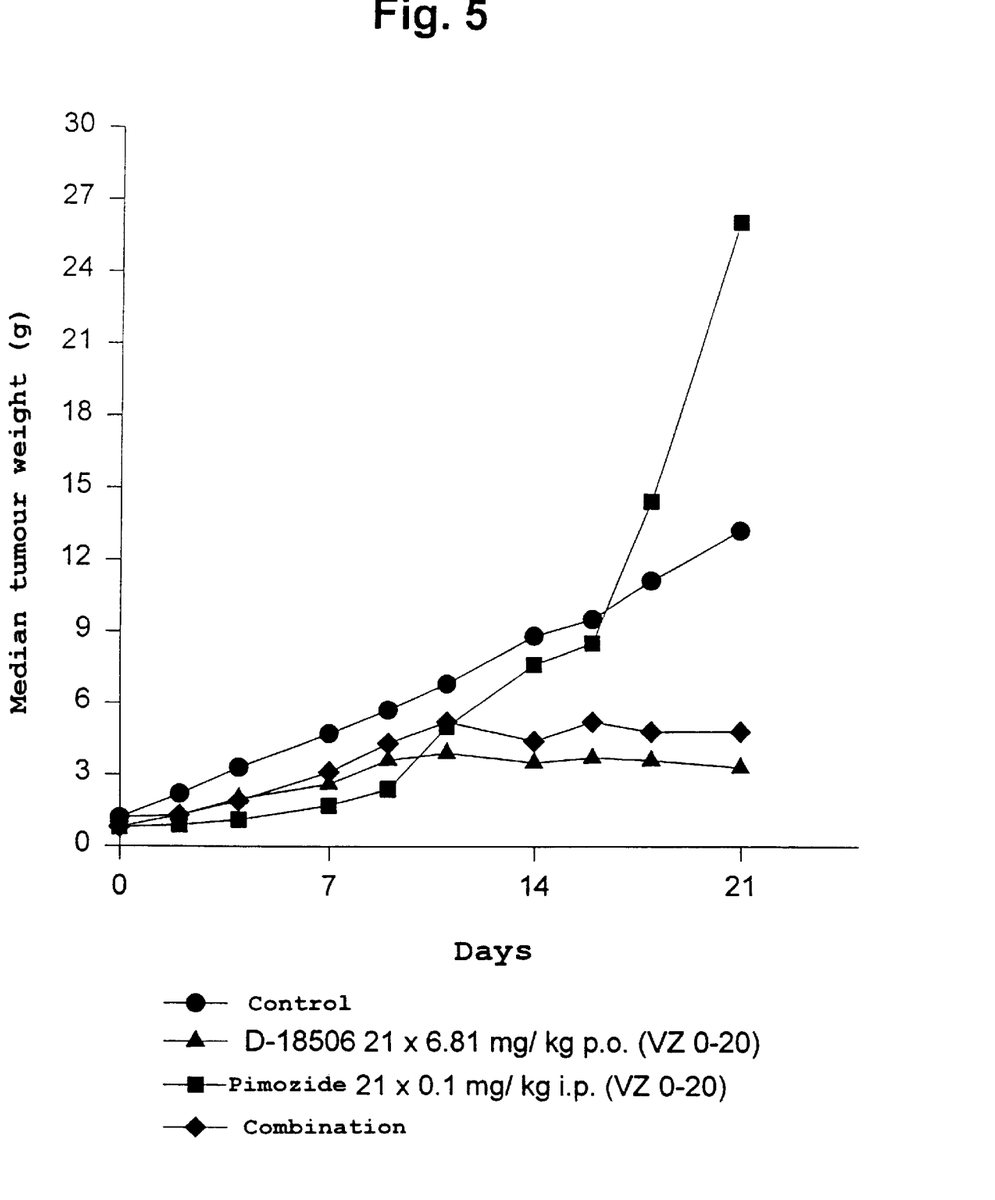
FIG. 5 shows effects of D-18506 (miltefosine) and pimozide on DMBA-induced breast tumor of rats.

Comparative studies with respect to body weight changes in healthy and tumor-bearing rats were investigated after administration of miltefosine or octadecyl (1,1-dimethylpiperidinio-4-yl) phosphate alone and in combination with various appetite stimulating compounds. On administration of miltefosine alone, there is a clear loss of weight in the two groups of animals. This is significantly antagonized by the simultaneous administration of domperidone (5×0.1 mg/kg i.p.) or pimozide (5×0.1 mg/kg i.p.) (dopamine antagonists). These effects are observed both in healthy and in tumor-bearing animals (FIGS. 1–3; Table 1). The anti-tumor action of miltefosine is not affected in combination with the two antidotes (FIGS. 4 and 5).

TABLE 1

Changes of body weight (rat)

| | | Control AUC | | D-18506(4 × 68.1 mg/kg p.o.) AUC | |
|---|---|---|---|---|---|
| | | day | | | |
| | mg/kg i.p. | 7 | 11 | 7 | 11 |
| | | 6.2 | 22.4 | −17.9 | −23.5 |
| Domperidone | 0.1 | 28.6** | 62.8** | 28.6** | 62.8 |
| Domp. + D-18506 | | 2.7 | 10.2 | 2.7** | 10.2* |

TABLE 1-continued

Changes of body weight (rat)

| | | Control AUC | | D-18506(4 × 68.1 mg/kg p.o.) AUC | |
|---|---|---|---|---|---|
| | | day | | | |
| | mg/kg i.p. | 7 | 11 | 7 | 11 |
| | | 6.2 | 22.4 | −17.9 | −23.5 |
| Pimozide | 0.2 | 30.4** | 69.8** | 30.4** | 69.8** |
| Pimo. + D-18506 | | 4.6 | 12.4 | 4.6 | 12.4 |
| Metoclopramide | 0.2 | 11.5 | 30.5 | 11.5** | 30.5** |
| Meto. + D-16506 | | −21.4 | −36.6 | −21.4 | −36.6 |
| Cyproheptadine | 2.5 | 0.8 | 15.5 | 0.8 | 15.5 |
| Cypro. + D-18506 | | −30.1 | 57.6 | −30.1 | −57.6 |

ACU = Area under the curve
Dunnett's T test for variable (AUC)
**p < 0.05 in comparison with the control group
*p < 0.10

The decrease in weight in the healthy and tumor-bearing animals which received miltefosine in combination with the dopamine receptor antagonists domperidone or pimozide turns out to be significantly lower than in the rats only treated with miltefosine. The control value (placebo-treated animals), however, is not reached.

Figure 6:
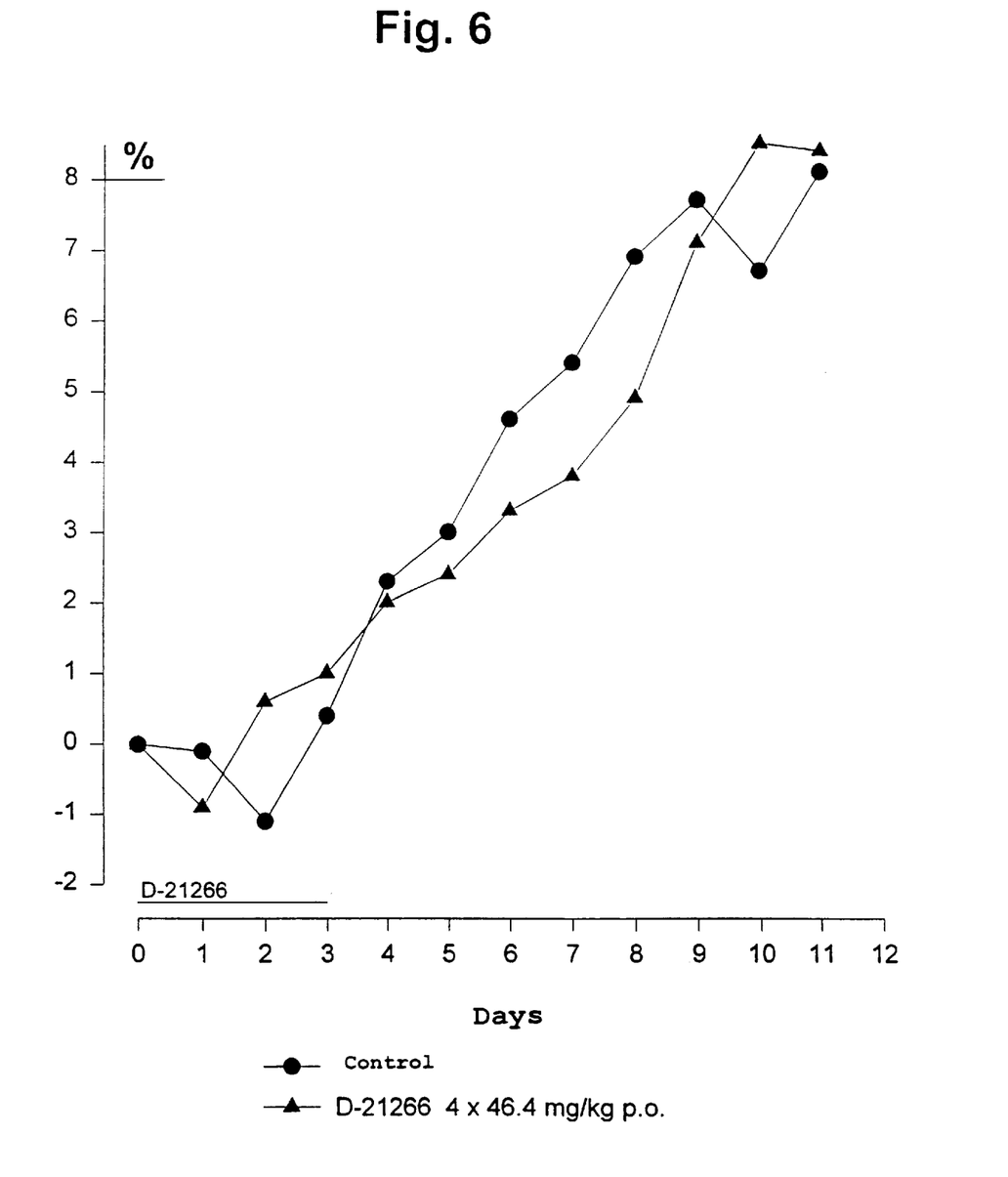
FIG. 6 shows effects of D-21266 (octadecyl (1,1-dimethylpiperidinio-4-yl)phosphate) on the body weight of normal rats.
Figure 7:
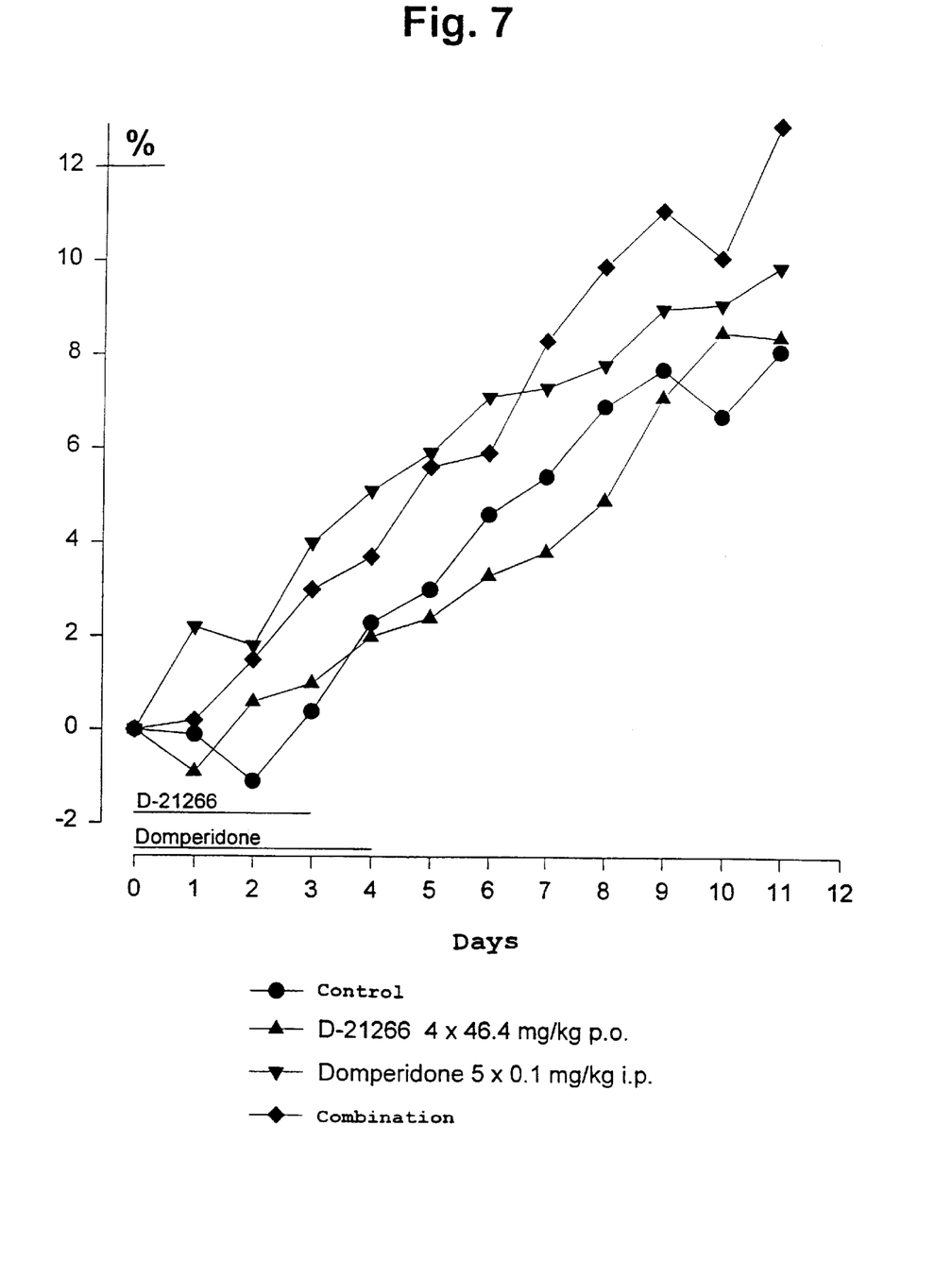
FIG. 7 shows effects of D-21266 (octadecyl (1,1-dimethylpiperidinio-4-yl)phosphate) and domperidone on the body weight of normal rats.
Figure 8:
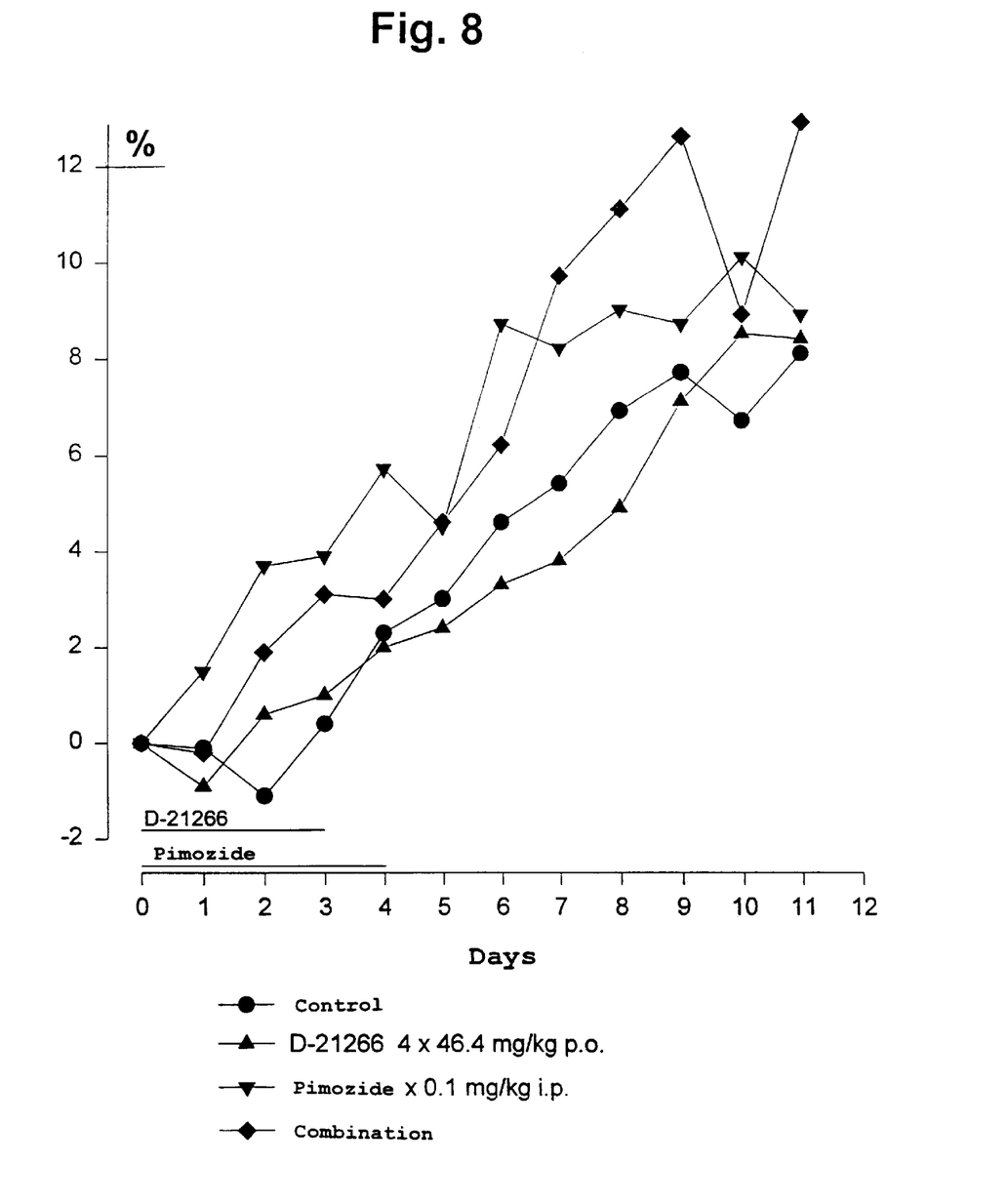
FIG. 8 shows effects of D-21266 (octadecyl (1,1-dimethylpiperidinio-4-yl)phosphate) and pimozide on the body weight of normal rats.
Figure 9:
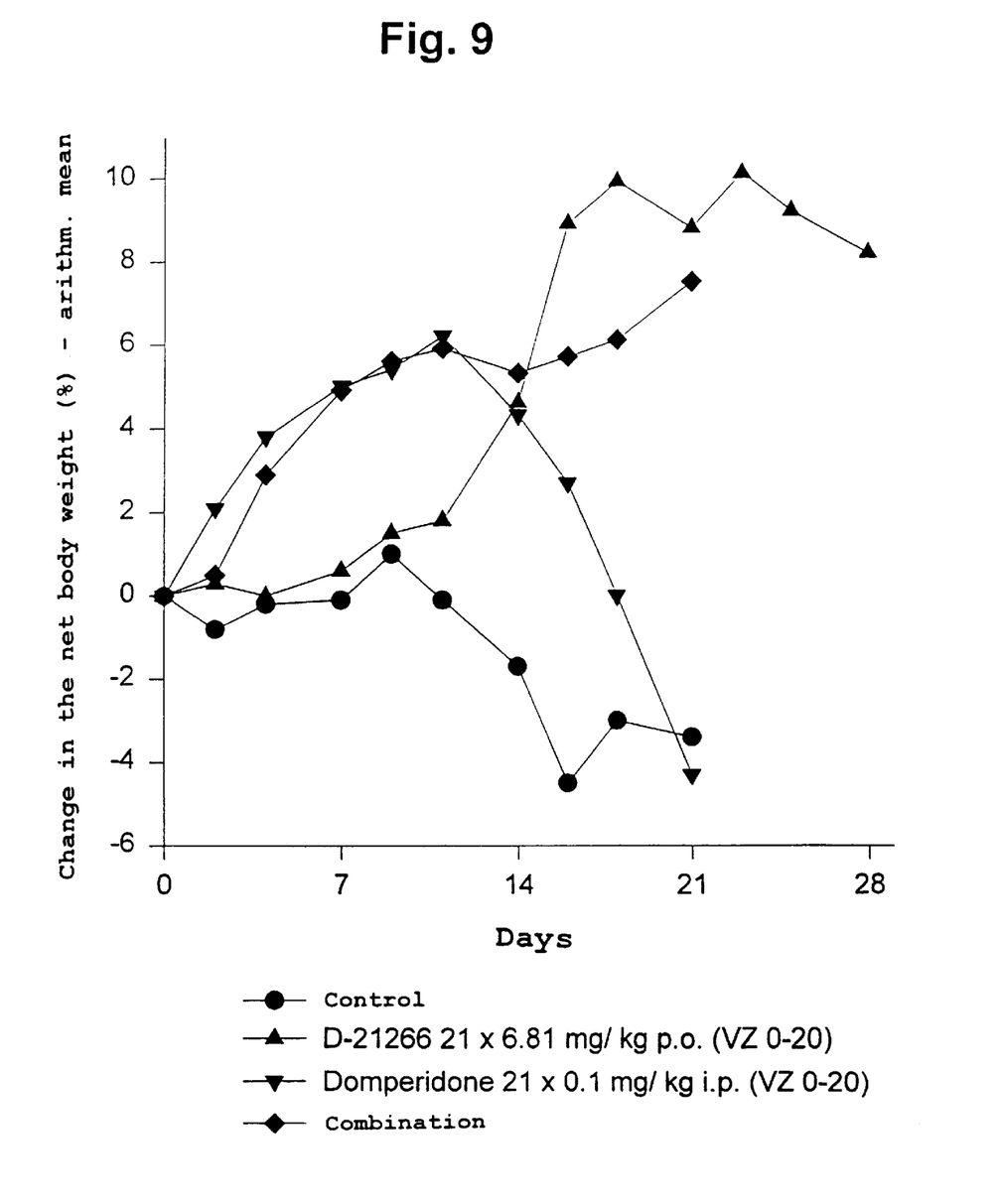
FIG. 9 shows effects of D-21266 (octadecyl (1,1-dimethylpiperidinio-4-yl)phosphate) and domperidone on the body weight of rats with DMBA-induced breast tumor.
Figure 10:
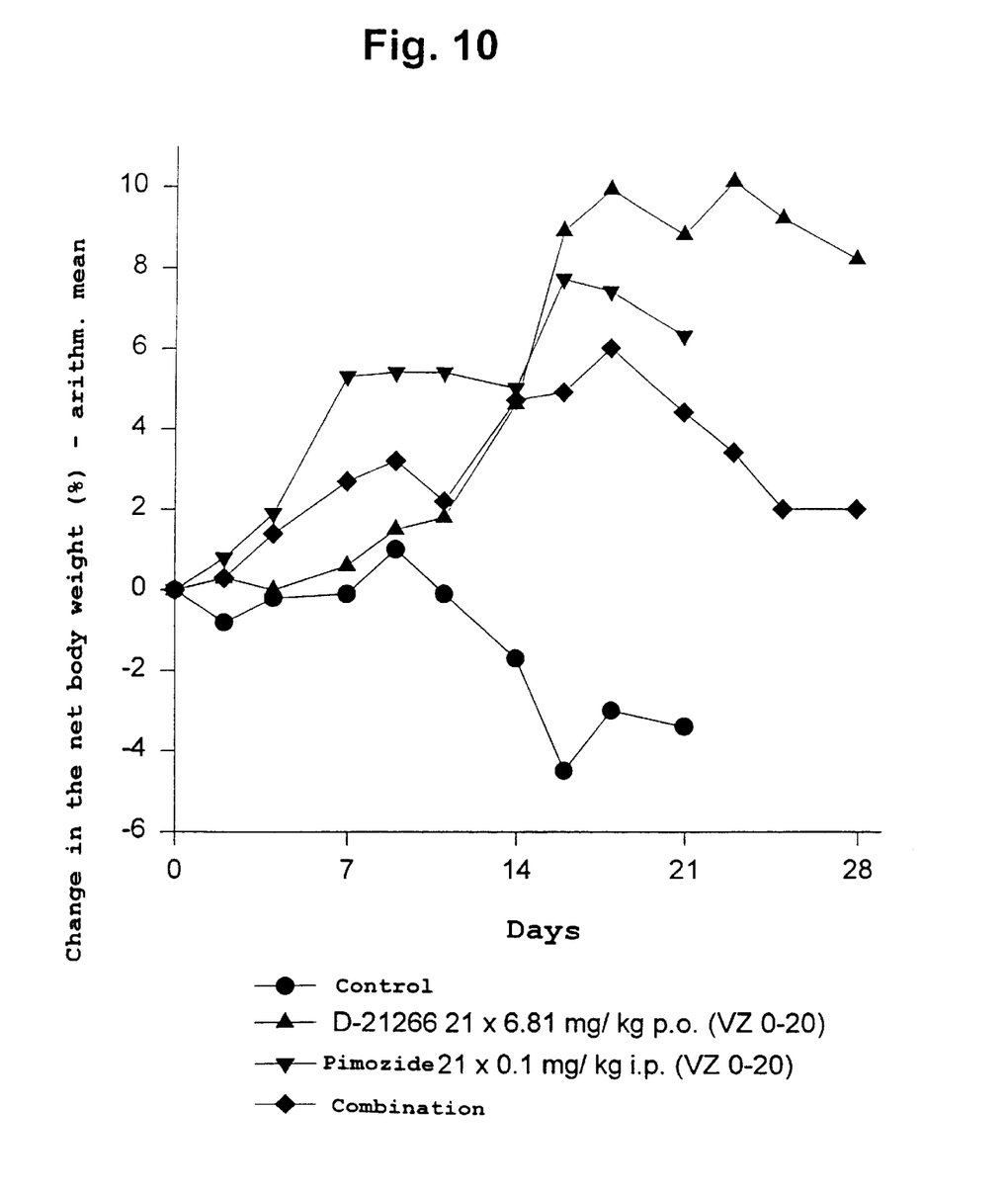
FIG. 10 shows effects of D-21266 (octadecyl (1,1-dimethylpiperidinio-4-yl)phosphate) and pimozide on the body weight of rats with DMBA-induced breast tumor.
Figure 11:
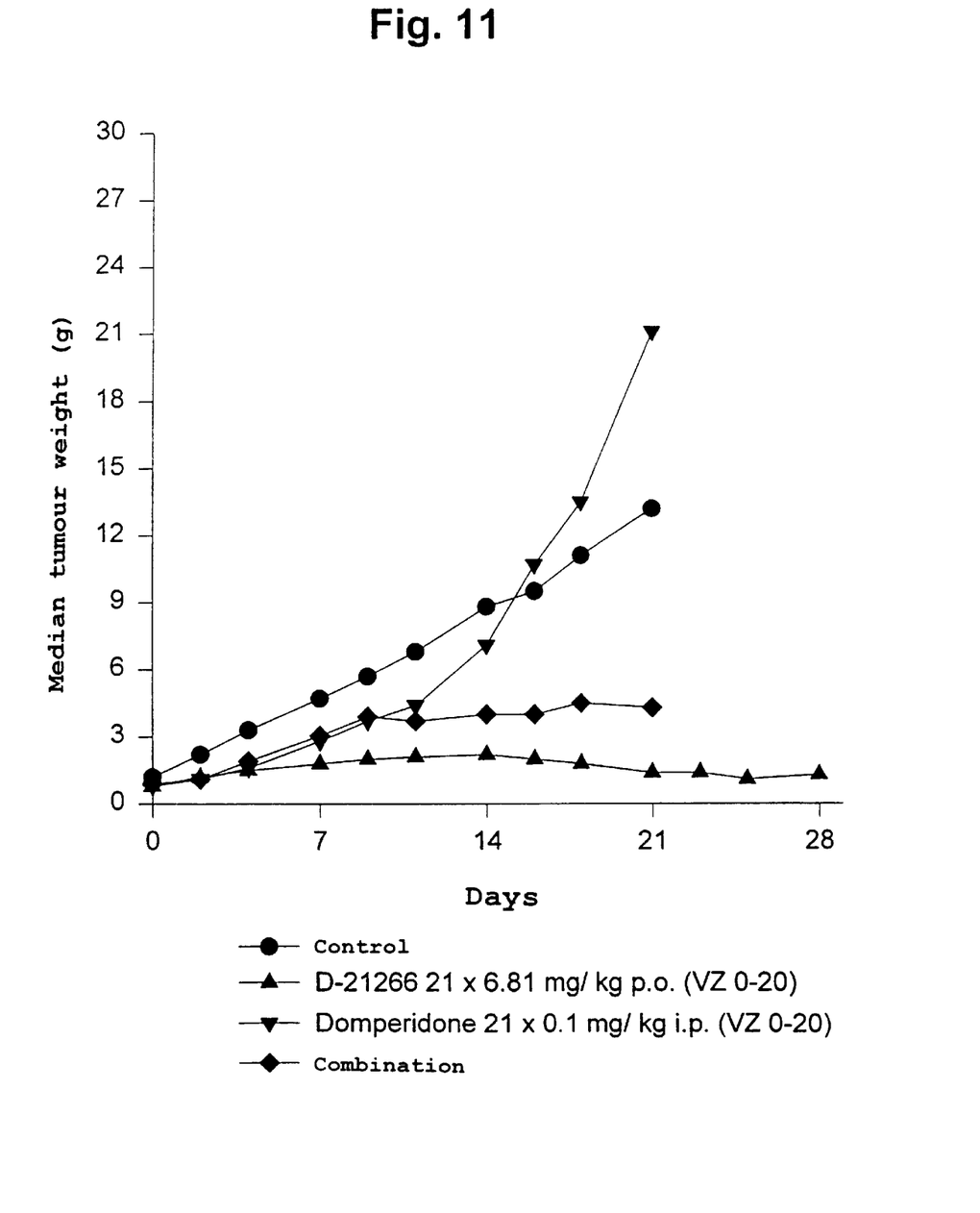
FIG. 11 shows effects of D-21266 (octadecyl (1,1-dimethylpiperidinio-4-yl)phosphate) and domperidone on DMBA-induced breast tumor in rats.
Figure 12:
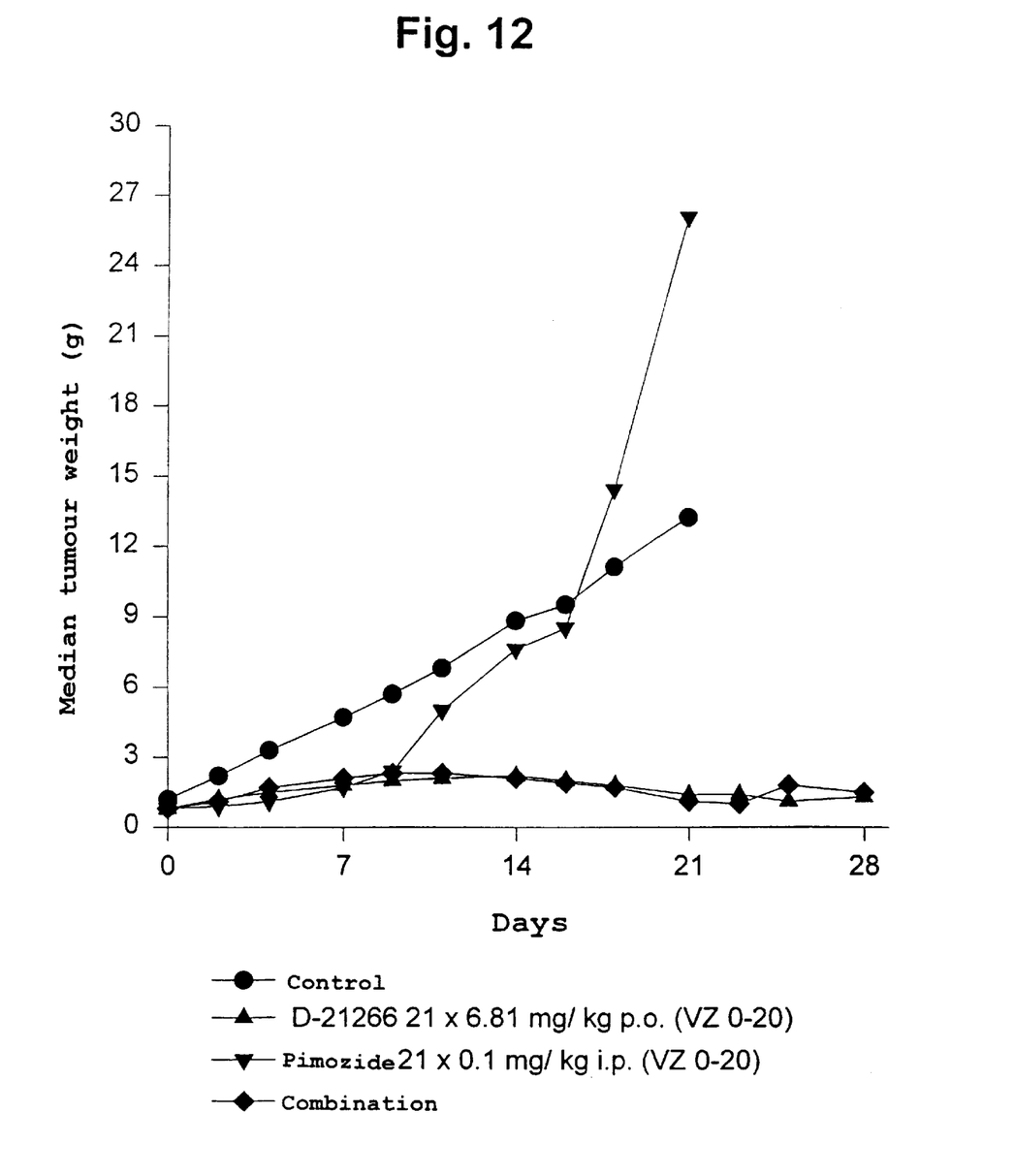
FIG. 12 shows effects of D-21266 (octadecyl (1,1-dimethylpiperidinio-4-yl)phosphate) and pimozide on DMBA-induced breast tumor in rats.

After administration of the alkylphosphocholine derivative octadecyl (1,1-dimethylpiperidinio-4-yl)-phosphate, there is a lower loss of weight in the with miltefosine. The rats increase in weight less than the control animals (FIG. 6). By the simultaneous administration of the dopamine receptor antagonists domperidone or pimozide, the slower increase in weight of the animals treated with octadecyl (1,1-dimethylpiperidinio-4-yl)phosphate is more than compensated. The animals are actually markedly heavier than the control animals only treated with placebo (FIGS. 7 and 8).

The two other appetite-stimulating compounds cyproheptadine and metoclopramide (serotonin receptor antagonists) in combination with octadecyl (1,1-dimethylpiperidinio-4-yl)phosphate had no significant effect on the body weight development of the animals (Table 2).

TABLE 2

Changes of body weight (rat)

| | | Control AUC | | D-21266(4 × 46.4 mg/kg p.o.) AUC | |
|---|---|---|---|---|---|
| | | day | | | |
| | mg/kg i.p. | 7 | 11 | 7 | 11 |
| | | 11.8 | 39.8 | 10.6 | 37.1 |
| Pimozide | 0.1 | 31.2** | 67.5** | 31.2** | 67.5** |
| Pimo. + D-21266 | | 23.5 | 67.3** | 23.5* | 67.3** |
| Cyproheptadine | 2.5 | 1.5 | 20.6 | 1.5 | 20.6 |
| Cypro. + D-21266 | | −18.1 | −41.2 | 18.1 | −41.2 |
| Metoclopramide | 0.2 | 19.2 | 49.4 | 19.2 | 49.4 |
| Meto. + D-21266 | | 18.4 | 46.6 | 18.4 | 46.6 |

TABLE 2-continued

Changes of body weight (rat)

| | | Control AUC | | D-21266(4 × 46.4 mg/kg p.o.) AUC | |
|---|---|---|---|---|---|
| | | day | | | |
| | mg/kg i.p. | 7 | 11 | 7 | 11 |
| | | 11.8 | 39.8 | 10.6 | 37.1 |
| Domperidone | 0.1 | 28.6** | 62.8** | 28.6** | 62.8** |
| Domp. + D-21266 | | 27.9** | 66.1** | 27.9** | 66.1** |

ACU = Area under the curve
Dunnett's T test for variable (AUC)
**p < 0.05 in comparison with the control group
*p < 0.10

In tumor-bearing animals, the same picture results as in healthy animals. Domperidone and pimozide alone and in combination with octadecyl (1,1-dimethylpiperidinio-4-yl) phosphate increase the body weight development of the animals without affecting the anti-tumor action (FIGS. 9–12).

The doses of the antidote were selected such that the compounds themselves caused no side effects at all in the experimental animals.

These results are surprising since the combination of miltefosine with the similarly appetite-stimulating substances metoclopramide or cyproheptadine does not lead to any positive effect on the decrease in weight in the animals. In contrast, there is instead an increase in the loss of weight (Table 1). A therapeutic use of dopamine receptor antagonists such as pimozide or domperidone was also in no way suggested by the contradictory statements in the art with respect to the effect on nemesis and nausea.

What is claimed is:

1. A composition comprising an amount of miltefosine therapeutically effective for treatment of a cancer sensitive to miltefosine, domperidone in an amount effective to reduce a side effect of said miltefosine and a pharmaceutically acceptable carrier, wherein said cancer is not sensitive to domperidone.

2. A dose unit of a pharmaceutical composition comprising an amount of miltefosine therapeutically effective for treatment of a cancer sensitive to miltefosine and domperidone in an amount effective to reduce a side effect of said miltefosine, wherein said cancer is not sensitive to domperidone.

3. A dose unit according to claim 2 comprising up to about 300 mg of miltefosine and about 10 to about 120 mg of domperidone.

4. A dose unit according to claim 1 comprising about 30 mg of domperidone.

5. A method of treating a side effect of miltefosine in a mammal being administered miltefosine for a cancer sensitive to miltefosine comprising administering to said mammal domperidone in an amount effective to reduce a side effect of an amount of miltefosine therapeutically effective for said cancer, wherein said cancer is not sensitive to domperidone.

6. A method according to claim 5 wherein the administration is simultaneous.

7. A method according to claim 5 wherein said amount of miltefosine is up to about 300 mg of miltefosine and about 10 to about 120 mg of domperidone is administered.

8. A method according to claim 7 wherein about 30 mg of domperidone is administered.

* * * * *